United States Patent
Papari

[19]

[11] Patent Number: 6,120,743
[45] Date of Patent: Sep. 19, 2000

[54] HYGIENIC SANITARY NAPKIN DISPOSAL SYSTEM

[76] Inventor: Joanne Papari, 1561 Rebecca Court, Mississauga, Ontario, Canada, L5M 4V9

[21] Appl. No.: 09/042,865

[22] Filed: Mar. 17, 1998

[51] Int. Cl.[7] ................................................ A61L 2/00
[52] U.S. Cl. .................... 422/300; 206/438; 206/567; 220/87.1; 220/908; 422/292
[58] Field of Search ................................. 422/300, 297, 422/292; 206/205, 210, 568, 581, 363, 438, 440, 567; 220/244, 252, 780, 87.1, 908

[56] References Cited

U.S. PATENT DOCUMENTS

| | | |
|---|---|---|
| 3,036,758 | 5/1962 | Greenbank et al. . |
| 4,601,880 | 7/1986 | Wong et al. ................................. 422/28 |
| 5,080,251 | 1/1992 | Noack . |
| 5,154,345 | 10/1992 | Shillington . |
| 5,287,960 | 2/1994 | Kalb et al. ................................. 206/210 |
| 5,482,208 | 1/1996 | Johnston . |
| 5,494,186 | 2/1996 | Marsh ....................................... 220/481 |
| 5,611,450 | 3/1997 | DeMars ..................................... 220/334 |
| 5,783,544 | 7/1998 | Trinh et al. ............................... 510/293 |
| 5,799,909 | 9/1998 | Ziegler ..................................... 248/101 |
| 5,881,896 | 3/1999 | Presnell et al. .......................... 220/252 |

FOREIGN PATENT DOCUMENTS 2114864   8/1994   Canada .

*Primary Examiner*—Krisanne Thornton
*Attorney, Agent, or Firm*—Notaro & Michalos P.C.

[57] ABSTRACT

A disposal system for the convenient and hygienic disposal of sanitary napkins detoxifies, sanitizes and deodorizes the sanitary napkins and prevents viewing of the unsightly disposed waste. The disposal system includes a secure rugged box-like container assembly having an opening at the top and a cover that fits over the opening. The cover has an access opening at the top and a lid pivotably securable to the cover, the lid formed in the shape of a wedge-shaped scoop, pivotal within the opening in the cover between a fully closed position that substantially seals the container to reduce evaporation and a fully opened position that permits waste material to be deposited into the container, prevents viewing of the contents of the container and controls any splashing. The disposal system includes a government-approved germicidal solution within the container, the solution including a blend of organic quaternary ammonium compound, isopropyl alcohol and fragrance.

6 Claims, 4 Drawing Sheets

HYGIENIC SANITARY NAPKIN DISPOSAL SYSTEM

FIELD OF INVENTION

The invention relates to disposal systems for the hygienic disposal of sanitary napkins.

BACKGROUND OF THE INVENTION

The hygienic disposal of sanitary napkins presents a serious problem for most public washroom facilities. Disposal of sanitary napkins via the normal sewage system is not practical since bulky sanitary napkins tend to plug drainage pipes and cause backups and blockages. As a result sanitary napkins can accumulate in regular waste receptacles of public washrooms. This causes serious problems with odour and can be a potential source of infection and disease if not dealt with effectively.

Various systems have therefore been developed in an attempt to deal with sanitary napkin waste disposal in public washroom facilities. The products currently available generally consist of storage containers separate from regular washroom waste receptacles. Such containers may be floor-standing or recessed into the washroom wall and generally have flip-top lids or flaps through which waste material is deposited into the container. In some cases the containers may contain a disinfecting solution for killing germs and bacteria and for reducing odours associated with such waste material.

The systems currently available, do not provide a secure, controlled environment for the disposal of sanitary napkins. Many of the current systems do not deal effectively with the associated odours and bacteria created by the disposal of sanitary napkins. If disinfecting solutions are used, they are often toxic and dangerous, especially considering that they are not generally contained in a rugged, secure, water-proof container spillage and splashing of the solution can create a danger to those using the container to dispose of waste and especially to those cleaning waste from the container. The current systems also do not function to effectively control and prevent viewing of the unsightly mess associated with the disposal of sanitary napkins. Opening the container to deposit waste often presents the washroom patron with an unpleasant visual image, a characteristic of sanitary napkin disposal that causes many people to simply flush the sanitary napkin down the toilet.

The lids on many of the current systems also have a tendency to become contaminated with waste fluids, thus presenting a risk of disease and infection to washroom patrons who must touch soiled portions of the lid in order to place waste material into the container.

SUMMARY OF THE INVENTION

It is therefore an object of the present invention to provide an improved disposal system for the hygienic disposal of sanitary napkins.

It is another object of the present invention to provide a disposal system that can be used in public washroom facilities that provides a rugged, secure and controlled environment for the hygienic disposal of sanitary napkins.

It is a further object of the present invention to provide a sanitary napkin disposal system that eliminates exposure of the washroom patron to the unsightly visual appearance of sanitary napkin waste.

It is a further object of a preferred embodiment of the present invention to provide a sanitary napkin disposal system that incorporates a non-toxic, government-approved germicidal solution to kill bacteria associated with soiled sanitary napkins and to eliminate unpleasant odours.

It is another object of the present invention to provide a disposal system for sanitary napkins that can remain in use for extended periods before requiring service.

It is yet another object of the present invention to provide a disposal system for sanitary napkins that is inexpensive to manufacture, easy to use and provides a cost-effective method for the safe and effective disposal of sanitary napkins.

According to the present invention, there is provided a sanitary disposal system comprising: a container for storing waste material, the container having a first opening; a cover for the first opening, the cover having a second opening; and a lid comprising top and bottom surfaces defining a receptacle, the lid being attached to the cover such that the lid is pivotable within the second opening between an open position wherein the bottom surface covers the second opening and the receptacle is positioned to receive waste material, and a closed position wherein the top surface covers the second opening and the receptacle is positioned to deposit waste material into the container.

In a preferred embodiment of the present invention there is provided a generally box-like container moulded from plastic, open at the top and containing a disinfecting solution. The container has a top cover with an opening and a wedge-shaped lid pivotally secured to the top cover so that it may be removed only with the use of special tools. The lid is pivotal within the opening in the top cover between a fully opened position that provides access to the container for placing waste therein yet prevents viewing of the contents of the container, and a fully closed position wherein waste material that has been placed on the inside surface of the lid is automatically deposited into the container and the container is substantially sealed to prevent splashing and reduce evaporation of the disinfecting solution within the container. The top cover includes a lip that extends horizontally into the opening and slops downward into the container. The lip is positioned to limit rotation of the lid between the fully opened position and the fully closed position and to prevent viewing of the contents of the container during the rotation of the lid between the fully opened position and the fully closed position.

Other advantages, objects and features of the present invention will be readily apparent to those skilled in the art from a review of the following detailed descriptions of a preferred embodiment in conjunction with the accompanying drawings and claims.

BRIEF DESCRIPTION OF THE DRAWINGS

Preferred embodiments of the present invention will now be described in greater detail, and will be better understood when read in conjunction with the following drawings, in which.

Similar reference numerals are used in different figures to denote similar components.

DETAILED DESCRIPTION OF THE INVENTION

Figure 1:
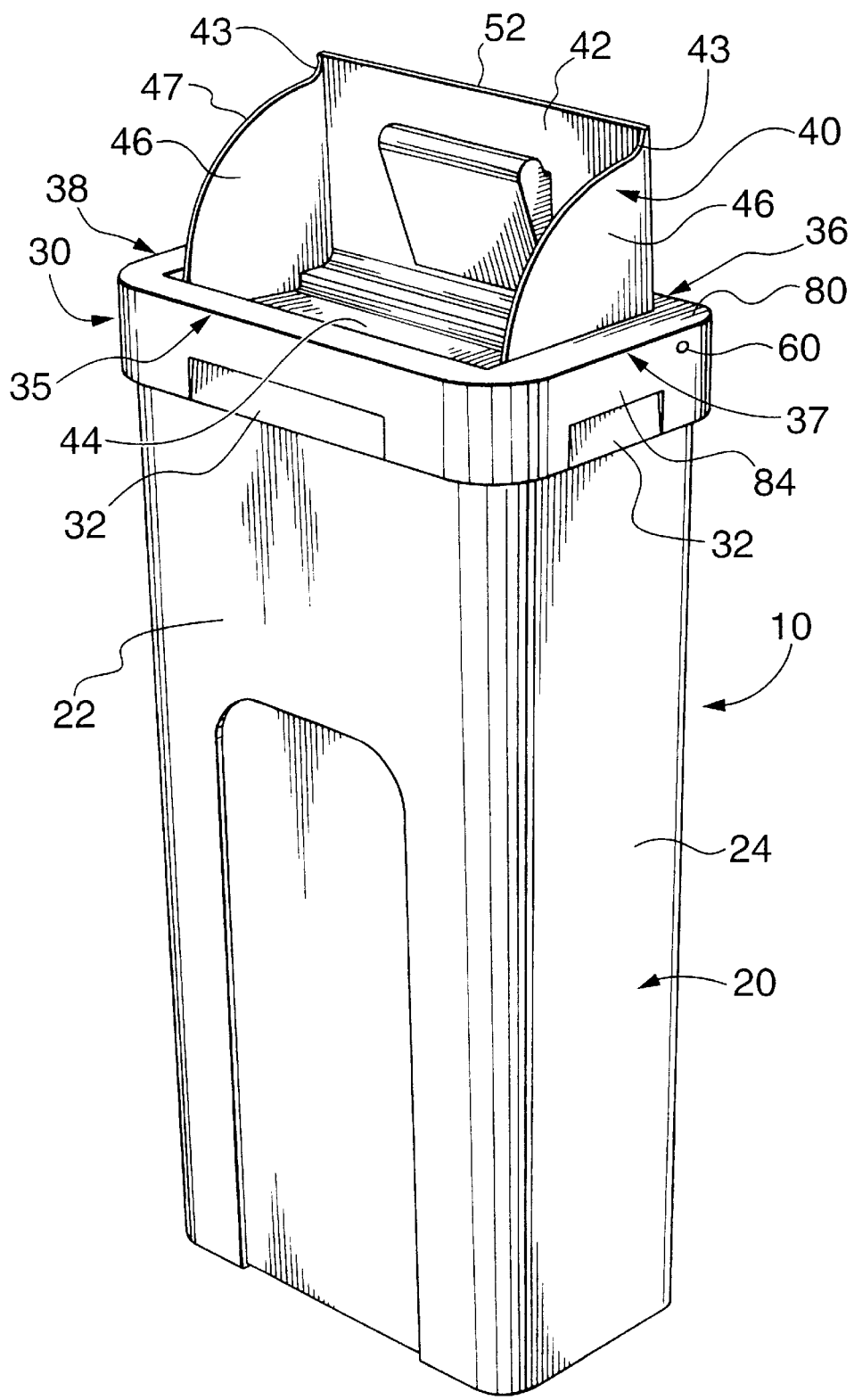
FIG. 1 is a front perspective view of one embodiment of the present invention with the lid fully open.

Referring to FIGS. 1 to 4, a hygienic sanitary napkin disposal system 10 comprises a water proof, generally box-like container 20 open at the top and closed at the bottom. Container 20 in its generally preferable form is formed of a substantially rectangular shell having a front wall 22, a back wall 23 and opposed side walls 24, all terminating in a top rectangular peripheral edge 25. Back wall 23 can be moulded to include an indentation 28 near the top that provides a convenient hand grip for use in carrying the invention or emptying the contents of container 20. It will be readily apparent that many equally effective alternatives to indentation 28 may be used to provide a hand grip, such as a raised ridge or a knob or handle secured to back wall 23.

Figure 3:
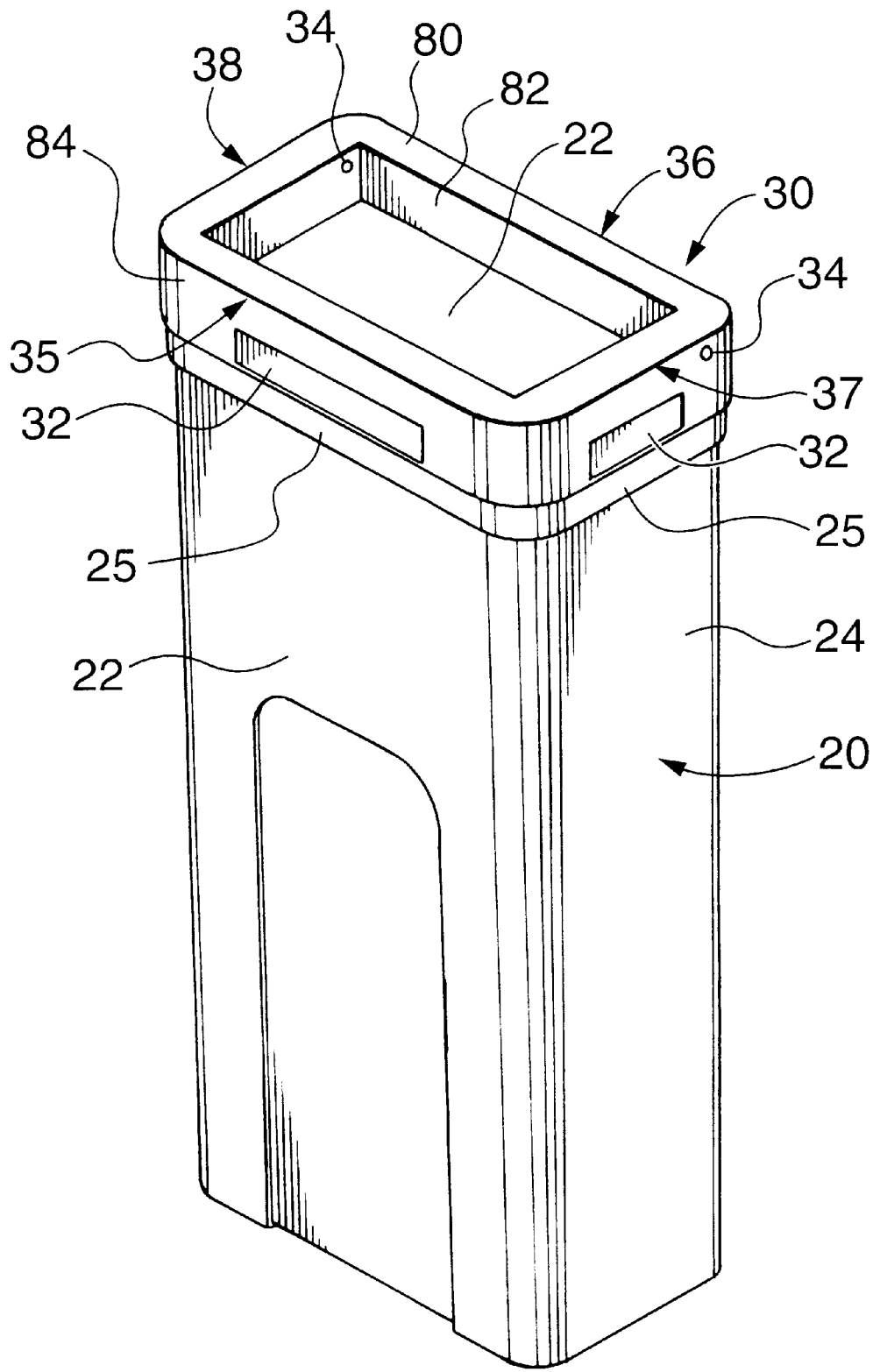
FIG. 3 is a front perspective view of the embodiment of the present invention as shown in FIG. 1, absent the lid.

The hygienic sanitary napkin disposal system 10 has a top cover 30 formed separately from container 20. In its generally preferable form, top cover 30 is substantially rectangular and of the same general outer dimension as the top rectangular peripheral edge 25 of container 20. Top cover 30 has a front edge 35, a back edge 36 and opposed side edges 37 and 38. As shown in FIG. 3, each of edges 35, 36, 37 and 38 of top cover 30 has a planer horizontal top surface 80, a planer vertical inside surface 82 and a planer vertical outside surface 84. The inside surface 82 and outside surface 84 of edges 35, 36, 37 and 38 are separated by a space thereby creating a channel (not shown) that runs completely around the periphery of the underside of top cover 30. This channel is of sufficient width to accommodate the top peripheral edge 25 of container 20. Top cover 30 is securely fit over the top of container 20 by fitting the top peripheral edge 25 of container 20 into the channel formed between the inside surface 82 and outside surfaces 84 of edges 35, 36, 37 and 38. Top cover 30 has a central rectangular opening 22 as shown in FIG. 3 that permits access to the interior of container 20. Each vertical outside surface 84 of edges 35, 36, 37 and 38 of top cover 30 may be formed with an horizontal indented handle 32 that can be used for transporting the invention or to facilitate the removal of top cover 30 from the top of container 20. Each of inside surface 82 and outside surface 84 of opposed side edges 37 and 38 of top cover 30 has a hole 34 (see FIG. 3) drilled through at a location near the back edge 36. When top cover 30 is securely fit over the top peripheral edge 25 of container 20, holes 34 line up with similar corresponding holes drilled through the top of side walls 24 of container 20. The purpose of these holes is to attach top cover 30 to container 20 as described in greater detail herein following.

Figure 4:
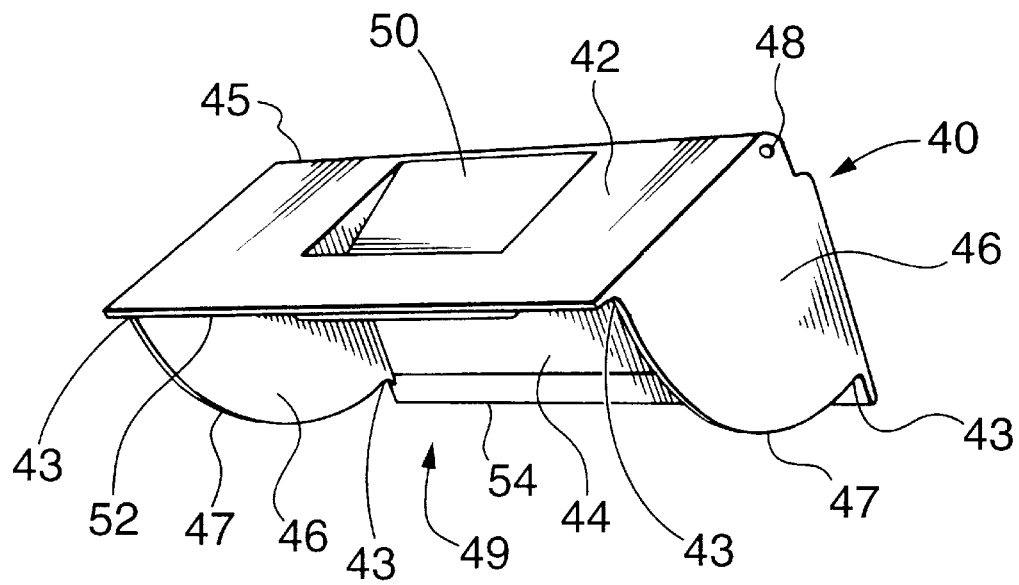
FIG. 4 is perspective view of the lid of the embodiment of the present invention as shown in FIGS. 1 and 2.

A lid 40, formed in the shape of a wedge-shaped scoop as shown in FIG. 4, is constructed to fit into opening 22 in top cover 30. Lid 40 comprises a rectangular front panel 42 and a rectangular back panel 44 joined along a common edge 45 to form a wedge shape and further joined by opposing triangular side panels 46 to form a wedge-shaped scoop or receptacle having an angular front opening 49 of less then 90 degrees. The outer edges 47 of side panels 46 are trimmed to a semi-circular shape to facilitate the pivoting of lid 40 within opening 22, thereby creating notches 43. Notches 43 define an exposed front edge 52 on front panel 42 and an exposed back edge 54 on back panel 44. The dimensions of lid 40 are slightly smaller than those of opening 22 so that lid 40 may freely pivot within opening 22. Each of side panels 46 has a hole 48 drilled through the side panel near common edge 45 where front panel 42 joins back panel 44.

Figure 2:
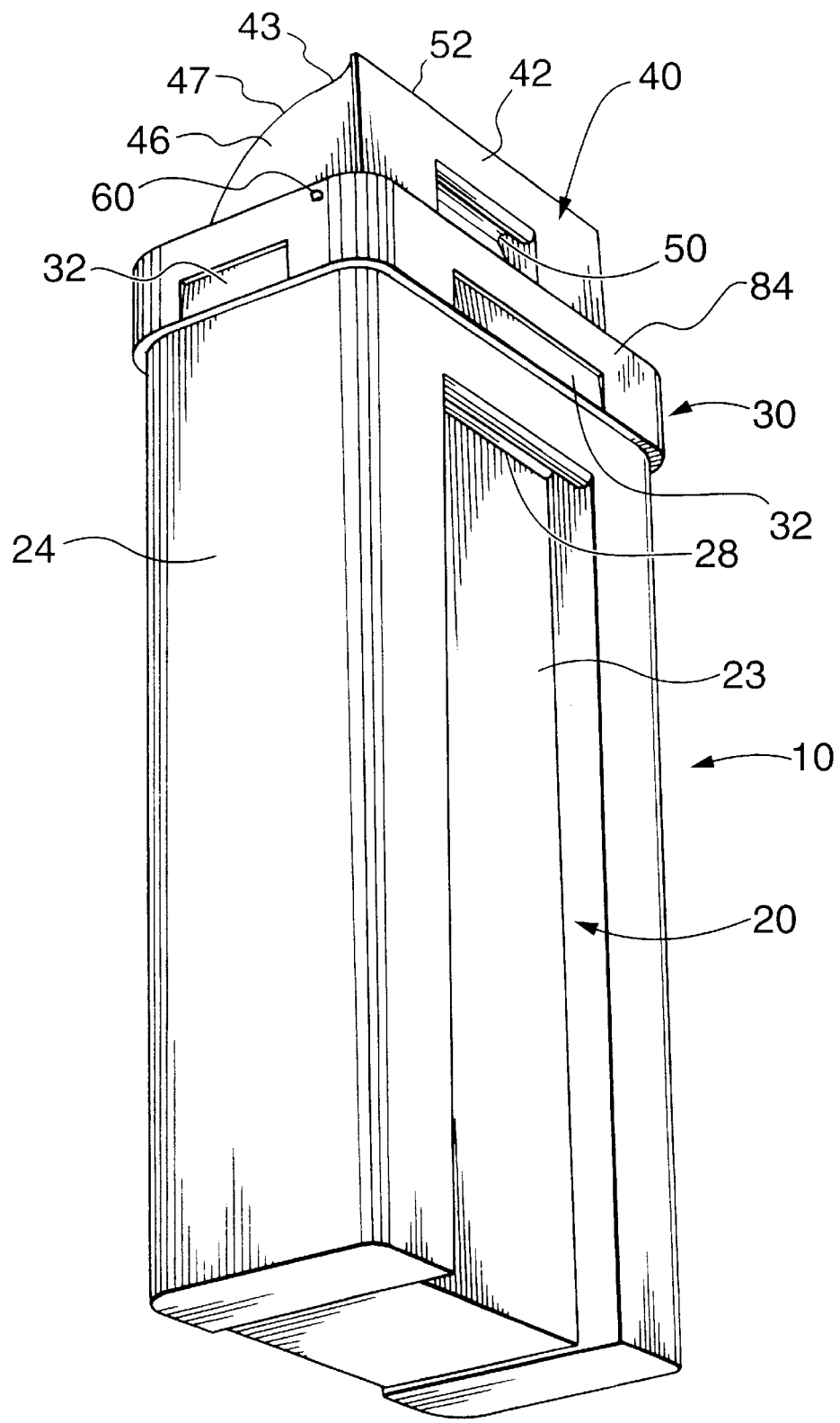
FIG. 2 is a rear perspective view of the embodiment of the present invention as shown in FIG. 1.
Figure 5:
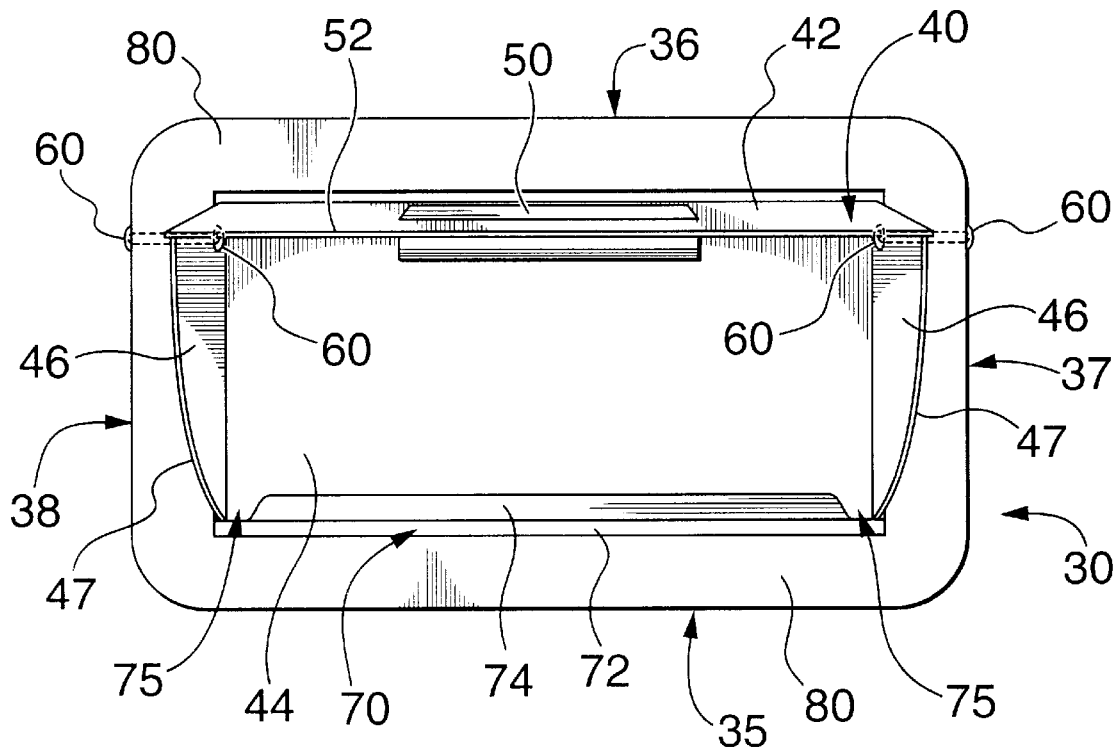
FIG. 5 is a top plan view of the embodiment of the present invention as shown in FIGS. 1 and 2, with the lid fully open.

When top cover 30 is securely fit over the top peripheral edge 25 of container 20 and lid 40 is fit into opening 22 as shown in FIGS. 1 and 2, holes 48 in lid 40 and holes 34 in top cover 30 line up with similar corresponding holes drilled through the top of side walls 24 near back wall 23 to permit the insertion of fasteners 60 (see FIG. 5) used to secure top cover 30 and lid 40 to container 20. Fasteners 60 are designed to permit lid 40 to pivot within opening 22 between a fully open position as shown in FIGS. 1, 2 and 5 and a normal, at rest, fully closed position where front panel 42 of lid 40 lies substantially parallel with the plane of opening 22. Fasteners 60 are not permanently attached but are constructed using known techniques so that they may only be removed using special tools not readily available. This ensures that access to the interior of the container is restricted to cleaning personnel only.

An indentation 50 is formed near the center of front panel 42 of lid 40. Indentation 50 is designed to provide a hand grip that can be used to grasp and open lid 40; however, it will be readily understood by someone skilled in the art that many different alternatives to indentation 50 are possible. For example, a knob or handle secured to front panel 42 would perform the same function.

Referring now to FIGS. 3 and 5, top cover 30 has a lip 70 located on the vertical inside surface of front edge 35. Lip 70 can be formed in a single piece and is comprised of a first lip 72 and a second lip 74. First lip 72 is attached directly to the vertical inside surface 82 of front edge 35 and extends laterally the entire length of front edge 35. First lip 72 is recessed just below the top surface 80 of front edge 35 by an amount equal to the thickness of top panel 42 of lid 40 and extends horizontally into opening 22 a short distance. The horizontal extension of first lip 72 into opening 22 is sufficient to hault the forward rotation of lid 40 on fasteners 60 within opening 22 by contact with the exposed front edge 52 of lid 40 such that lid 40 comes to rest in a fully closed position where front panel 42 of lid 40 lies substantially parallel with the plane of opening 22 and the top surface of front panel 42 is substantially on the same horizontal plane as the top surface 80 of edges 35, 36, 37 and 38 of top cover 30. Second lip 74 is connected to the inside edge of first lip 72 and extends laterally for almost the entire length of first lip 72, leaving small spaces 75 at each end to accommodate side panels 46 of lid 40 and permit the pivoting of lid 40 within opening 22. Second lip 74 extends a short distance horizontally from the inside edge of first lip 72 toward the center of opening 22 and is sloped at a downward angle in order to direct any fluids or waste material into container 20. Second lip 74 extends sufficiently into opening 22 to hault the backward rotation of lid 40 on fasteners 60 within opening 22 by contact with the exposed back edge 54 of lid 40 thus preventing further rotation of lid 40 beyond the fully open position shown in FIGS. 1, 2 and 5. Second lip 74 also extends laterally and horizontally into opening 22 an amount sufficient to prevent viewing of the contents of container 20 at any point during the rotation of lid 40 between the fully closed and the fully opened positions.

Container 20 is partly filled with a chemical disinfecting solution that is both a virucide and a germicide. Preferably the solution used is one registered and approved by a national or government regulatory agency for safe, non-toxic public use. The solution acts to detoxify, sanitize and deodorize waste material placed into the hygienic sanitary napkin disposal system 10 and can remain effective for up to two months. The solution is preferably non-toxic and non-corrosive and therefore has no adverse environmental or occupational effects.

Those skilled in the art will be aware of many such disinfecting solutions that could be effectively used in the present invention. The applicant has found that a blend of organic quaternary ammonium compound, isopropyl alcohol, water and fragrance is particularly effective. The organic quaternary ammonium compound, sometimes referred to as QUAT, can be any one of numerous strong bases and their salts derived from ammonium by replacement of the hydrogen atoms with organic radicals. QUAT is chemically stable at normal temperatures and pressures, is biodegradable and acts as a potent disinfectant. Isopropyl alcohol (Isopropanol) is a colourless organic solvent with a mild hydrocarbon odour. It is completely soluble in water, chemically stable and has no toxicity or carcinogenicity. The fragrance can be any non hazardous liquid with a strong characteristic odour. It is insoluble in water and chemically stable. Fragrance is used to counteract the foul smell of the washroom waste and the odour of chemicals used in the solution.

Although isopropyl alcohol has some mild disinfecting properties, its more important function in the solution used by the applicant in the present invention is as a solvent for the quaternary compound. Quaternary compound is more soluble in isopropyl alcohol than it is in water, therefore the disinfecting strength of the applicant's solution is significantly enhanced over that of a similar solution containing only quaternary compound and water. Isopropyl alcohol further acts to more effectively carry the quaternary compound into a vapour state within the container thus creating a strong disinfecting environment within the container to aid in the disinfection of any material deposited into the container that may not come into direct contact with the disinfecting solution. The combination of quaternary compound and isopropyl alcohol increases the germicidal effect of the quaternary compound and extends the life of the vapour action inside the hygienic sanitary napkin disposal system 10, thus providing a more powerful solution for destroying bacteria and microorganisms. Another important function of the isopropyl alcohol is that it makes the fragrance more miscible in water and further acts as a carrier to distribute the fragrance.

Test results conducted on sample swabs taken on a random basis from the interior of various hygienic sanitary napkin disposal systems show no detectable amounts of bacteria or any other microorganisms. Test result also show that an optimum amount of between four and five liters of disinfecting solution as described above will remain effective in the present invention for up to two months.

All components of the hygienic sanitary napkin disposal system 10 including container 20, top cover 30 and lid 40 may be constructed of hard plastic material moulded to the desired shape using known techniques. Other materials such as stainless steel, aluminum or glass may also be used provided they can be formed into the desired shape and made water proof to hold the liquid disinfecting solution. Bolt 60 is generally made of stainless steel; however any corrosion resistant metal or plastic may also be used.

The hygienic sanitary napkin disposal system 10 functions to effectively and hygienically dispose of sanitary napkins or other waste material in a manner as describe below. Lid 40 is constructed so that it automatically rotates forward on fasteners 60, under the force of gravity, to a normal, at rest, fully closed position substantially sealing opening 22 in top cover 30 limiting the escape of chemical vapours and odour from within container 20. In this fully closed position, exposed front edge 52 of lid 40 rests on first lip 72 of top cover 30 and front panel 42 is oriented substantially parallel with the horizontal plane of opening 22.

When it is desired to place waste material into the hygienic sanitary napkin disposal system 10, handle 50 is grasped with the fingers of one hand and lid 40 is rotated in a rearward direction on fasteners 60 to a fully open position as shown in FIGS. 1, 2 and 5. The pivoting of lid 40 on bolts fasteners 60 continues until exposed back edge 54 of lid 40 comes into contact with the underside of second lip 74 of top cover 30. In this fully open position, back panel 44 is oriented substantially parallel with the horizontal plane of opening 22 and presents a smooth horizontal surface on which waste material may be placed. Once the waste material has been placed on back panel 44, handle 50 is released and lid 40 is allowed to automatically rotate under the force of gravity in a forward direction and return to its normal, at rest fully closed position. The waste material is thus deposited into container 20 where it is immediately detoxified, sanitized and deodorized by the solution and the vapours contained therein. The solution and the vapours destroy any bacteria or infectious germs that may be present in or on the waste material and eliminate any unpleasant odours. Any splashing that may occur is effectively contained within the hygienic sanitary napkin disposal system 10 by the unique design of the scoop-shaped lid 40 and the extension of lip 70 into opening 22. Once lid 40 has returned to its normal, at rest fully closed position it functions to substantially seal the container limiting the escape of chemical vapours and any unpleasant odours. The chemical vapours thus trapped within container 20 continue to act as a disinfectant, killing germs and bacteria on any exposed surfaces or on any waste material within container 20 that might not be in direct contact with the disinfecting solution.

One particular unique advantage of the hygienic sanitary napkin disposal system herein described is that, regardless of the observation angle, it is not possible to view the contents of container 20 during the opening and closing of lid 40 between its fully closed position and its fully opened position as described above. This characteristic of the design of scoop-shaped lid 40 and cover 30 of the present invention also functions to effectively contain any splashing of any liquids completely within the hygienic sanitary napkin disposal system 10 and further prevents any contact between the waste material already in container 20 and any person depositing additional waste into container 20.

One further important advantage of the present hygienic sanitary napkin disposal system 10 is that a person depositing waste material need not come into contact with any soiled or potentially infected surfaces. A person depositing waste material touches only front panel 42 and handle 50 in order to raise lid 40 to expose the inside back panel 44. Front panel 42 and handle 50 should never come into contact with any waste material. Only the inside surfaces of back panel 44 and side panels 46 of lid 40 come into contact with waste material and these are therefore the only surfaces that will normally become soiled. The inside surfaces of back panel 44 and side panels 46 of lid 40 remain completely enclosed at all times when lid 40 is closed and are thus disinfected by the above-described chemical vapours within container 20.

Under normal operating conditions, fasteners 60 secure lid 40 and top cover 30 to container 20 allowing the free rotation of lid 40, preventing the removal of lid 40 and top cover 30 from container 20, thereby restricting access to the contents of container 20. When container 20 is full or after a period of up to two months when the solution is no longer effective, cleaning personnel use special tools to remove fasteners 60 and empty the contents of container 20. The chemical solution is then replenished and the sanitary napkin disposal system 10 is reassembled for further use.

The above-described embodiments of the present invention are meant to be illustrative of a preferred embodiment of the present invention and are not intended to limit the scope of the present invention. Various modifications, which would be readily apparent to one skilled in the field of hygienic disposal systems, are intended to be within the scope of the present invention without any departure from the spirit of the present invention. The appended claims, properly construed, form the only limitations to the scope of the present invention.

I claim:

1. A sanitary disposal system comprising:

a container for storing waste material, the container having a first opening;

a cover for the first opening, the cover having a second opening; and a lid comprising top and bottom surfaces defining a receptacle, the lid being attached to the cover such that the lid is pivotable within the second opening between an open position wherein the bottom surface covers the second opening and the receptacle is positioned to receive waste material, and a closed position wherein the top surface covers the second opening and the receptacle is positioned to deposit waste material into the container.

2. A sanitary disposal system according to claim 1 wherein the cover has a lip that extends horizontally into the receptacle.

3. A sanitary napkin disposal system according to claim 2 wherein the lip is angled downward for directing waste material into the container.

4. A sanitary napkin disposal system according to claim 1, wherein the lid is removably attached to the cover and the cover is removably attached to the container.

5. A sanitary napkin disposal system according to claim 1, further comprising a germicidal disinfecting solution contained within the container for killing bacteria and microorganisms.

6. A sanitary napkin disposal system according to claim 5, wherein the disinfecting solution is a blend of an organic quaternary ammonium compound with isopropyl alcohol, fragrance and water.

* * * * *